Sept. 2, 1947. W. I. JOHNSTON Plant Pat. 758
ROSE PLANT
Filed May 24, 1946
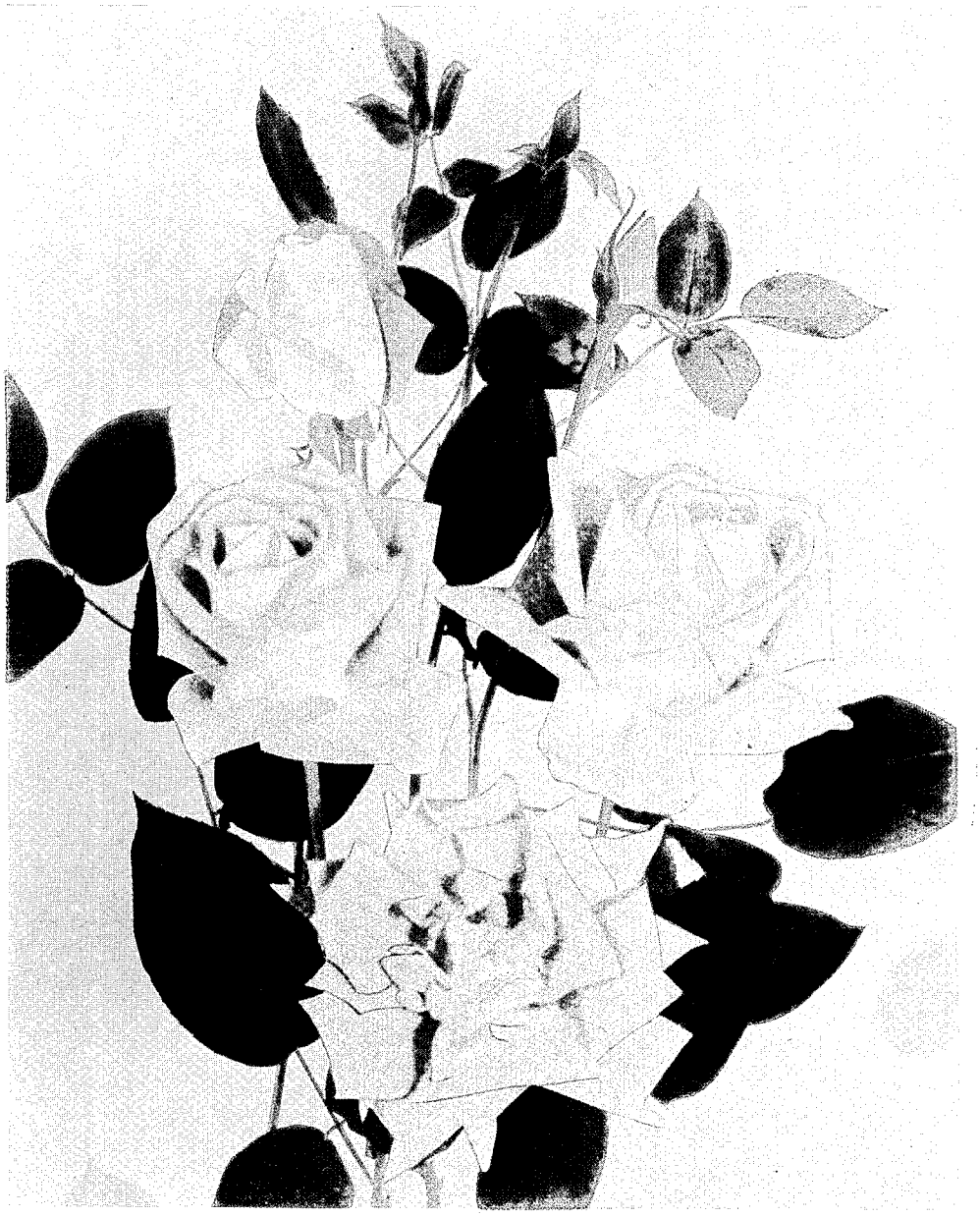
Inventor
W. I. Johnston
By Robbins Robb
Attorneys Patented Sept. 2, 1947

Plant Pat. 758

UNITED STATES PATENT OFFICE

758

ROSE PLANT

Walter I. Johnston, Portadown, Ireland, assignor to Jackson & Perkins Company, Newark, N. Y., a corporation of New York Application May 24, 1946, Serial No. 671,951

1 Claim. (Cl. 47—61)

The present invention relates to a new and distinct variety of hybrid tea rose plant, originated by the crossing of two unnamed seedlings.

This new variety has been tested under all conditions throughout the United States and all of these tests have shown it to be an unusually vigorous bush with free flowering habits.

It is further characterized as to novelty by the color of the flowers, Rose Red color on the inside of the petal and contrasting Rose Red overlaid with Rose color on the outside of the petals; by the very rich Old Rose fragrance of the blooms, quite unusual in roses of corresponding size and color; by the Light Cadmium anthers and Spectrum Red filaments; and by the large size bud and flower and very plentiful dark green foliage.

Asexual reproduction of this new variety shows the foregoing characteristics come true to form and are established.

In the drawings is illustrated a fair group specimen of the new variety showing the flowers at different stages of development from bud to fully opened bloom.

The following is a detailed description of the new variety, the color terminology being in accordance with Ridgway's Color Standard:

Parentage: Seedling.
*Seed parent.*—Unnamed seedling.
*Pollen parent.*—Unnamed seedling.
Classification: Botanic and commercial—hybrid tea.

*Flower*

(Observations made in the fields of Jackson & Perkins Company, Newark, New York, in the month of January, 1946.)

Blooming habit: Recurrent—continuous.
Bud:
*Size.*—Large.
*Form.*—Long; pointed. Is not affected by wet or hot weather.
*Color.*—When sepals first divide—Oxblood Red, Plate I. When petals begin to unfurl—Pomegranate Purple, Plate XII. When half blown—Inside of petals—Rose Red, Plate XII. Reverse of petals—Rose Color, Plate XII, overlaid with Deep Rose Pink, Plate XII.
*Sepals.*—Branched. Curl back when petals begin to unfurl. *Color*—inside—Light Cress Green, Plate 31. Outside—Light Elm Green, Plate 17.

*Calyx.*—*Shape*—urn. *Size*—small. *Aspect*—smooth. *Odor when rubbed*—none. *Color*—Lettuce Green, Plate 5.
*Peduncle.*—*Length*—long. *Aspect*—smooth. *Color*—Lettuce Green, Plate 5. *Strength*—erect; slender.
*Opening.*—Opens up well. Is not affected by adverse weather conditions.

Bloom:
*Size.*—Large. Average size when fully expanded—4½–5 inches.
*Borne.*—Several together.
*Stems.*—Long; strong.
*Form.*—When first open—high center. Permanence—flattens.
*Petalage.*—Double (full but open center). Number of petals under normal conditions—25.
*Color.*—Center of flower—Tyrian Rose, Plate 12. Outer petals—Tyrian Rose tinted with Rose Red, Plate 12. Base of petals (aiglet)—Light Greenish Yellow, Plate 5. Inside of petals—Rose Red, Plate 12. Reverse of petals—Rose Red overlaid with Rose Color, Plate 12. General tonality from a distance—Rose Red, Plate 12.
*Discoloration.*—General tonality at end of first day—Rose Red, Plate 12. Second day—Rose Red, Plate 12. Third day—Rose Red overcast with Tyrian Rose, Plate 12.

Petals:
*Texture.*—Thick. Is not affected by wet or hot weather.
*Appearance.*—Inside—velvety. Outside—shiny.
*Form.*—Oval.
*Arrangement.*—Imbricated (regularly arranged shingle-like). Petaloids in center—few; large.
*Persistence.*—Drop off cleanly.
*Fragrance.*—Strong. Nature—"Old Rose perfume" (Centifolia).
*Lasting quality.*—On the plant and as cut flower—long.

Genital organs:
*Stamens, Anthers.*—Large; many. Color—Light Cadmium, Plate 4. Arrangement—Regular around styles.
*Stamens, Filaments (threads).*—Long. Color—Spectrum Red, Plate I.
*Pollen.*—Apricot Yellow, Plate 4.

*Styles.*—Bunched, uneven length; long; heavy.
*Stigmas.*—Picric Yellow, Plate 4.
*Ovaries.*—All enclosed in calyx.

*Plant*

Form: Bush.
Growth: Very vigorous; upright; branching.
Foliage: 5 leaflets.
*Size.*—Large.
*Quantity.*—Abundant.
*Color.*—New foliage—upper side—Yellowish Oil Green, Plate 5, edges and mid-rib Oxblood Red, Plate I. Under side—Rainette Green, Plate 31, lightly overcast with Oxblood Red, Plate I. *Old foliage*—upper side—Dark Cress Green, Plate 31. Under side—Light Cress Green, Plate 31.
*Shape.*—Oval pointed.
*Texture.*—Upper side—leathery. Under side—Smooth. Ribs and veins—Prominent.
*Edge.*—Serrated (saw toothed).
*Serration.*—Single; small.
*Leaf stem.*—Grass Green, Plate 6. Under side—prickles.
*Stipules.*—Medium length; smooth.
*Disease Resistance.*—Good.

Wood:
*New wood.*—Color—Mars Brown, Plate 15. Bark—smooth.
*Old wood.*—Color—Cress Green, Plate 31. Bark—smooth.

Thorns (thorns are divided into thorns, prickles and short needles):
*Thorns.*—Quantity—On main stalks from base—many. On laterals from stalk—ordinary. Form—narrow base; medium length; hooked downward. Color when young—Corinthian Red, Plate 27. Position—irregular.
*Prickles.*—On main stalks and on laterals—none.
*Needles.*—On main stalks and on laterals—none.

I claim:

A new and distinct variety of rose plant of the Hybrid tea class, characterized as to novelty by its vigorous growing and free flowering habits; the large size of bud and flower; the very rich Old Rose fragrance of these flowers; the color combination of the flowers, anthers and filaments; and the plentiful amount of dark green foliage, substantially as shown and described.

WALTER I. JOHNSTON.